United States Patent [19]

Chin et al.

[11] Patent Number: 4,865,037
[45] Date of Patent: Sep. 12, 1989

[54] METHOD FOR IMPLANTING AUTOMATIC IMPLANTABLE DEFIBRILLATOR

[75] Inventors: Albert K. Chin; Thomas J. Fogarty, both of Palo Alto, Calif.

[73] Assignee: Thomas J. Fogarty, Palo Alto, Calif.

[21] Appl. No.: 120,590

[22] Filed: Nov. 13, 1987

[51] Int. Cl.⁴ .............................................. A61N 1/38
[52] U.S. Cl. ................................. 128/419 D; 128/786
[58] Field of Search ............ 128/419 D, 419 P, D 26, 128/786; 604/174, 175, 180

[56] References Cited

U.S. PATENT DOCUMENTS

| | | | |
|---|---|---|---|
| 3,663,965 | 5/1972 | Lee, Jr. et al. | 604/175 |
| 3,737,579 | 6/1973 | Bolduc | 128/418 |
| 3,749,101 | 7/1973 | Williamson | 128/418 |
| 3,866,615 | 2/1975 | Hewson | 128/419 D |
| 3,866,616 | 2/1975 | Purdy et al. | 128/419 |
| 3,942,536 | 3/1976 | Mirowski et al. | 128/419 |
| 3,987,799 | 10/1976 | Purdy et al. | 128/419 |
| 4,016,884 | 4/1977 | Kwan-Gett | 128/DIG. 26 |
| 4,026,302 | 5/1977 | Grayzel | 128/418 |
| 4,030,509 | 6/1977 | Heilman et al. | 128/419 |
| 4,270,549 | 6/1981 | Heilman | 128/784 |
| 4,291,707 | 9/1981 | Heilman et al. | 128/784 |
| 4,345,606 | 8/1982 | Littleford | 128/419 D |
| 4,355,642 | 10/1982 | Alferness | 128/642 |
| 4,355,646 | 10/1982 | Kallok et al. | 128/786 |
| 4,374,527 | 2/1983 | Iverson | 128/784 |
| 4,516,584 | 5/1985 | Garcia | 128/419 D |
| 4,548,203 | 10/1985 | Tacker, Jr. et al. | 128/419 D |
| 4,567,900 | 2/1986 | Moore | 128/784 |
| 4,672,979 | 6/1987 | Pohndorf | 128/419 P |
| 4,699,616 | 10/1987 | Nowak et al. | 604/180 |

FOREIGN PATENT DOCUMENTS

| | | | |
|---|---|---|---|
| 1184139 | 7/1959 | France | 128/DIG. 26 |
| 0048712 | 12/1987 | United Kingdom | 128/DIG. 26 |

OTHER PUBLICATIONS

"Elecath Cardiovascular Catheters and Instruments", 1972, p. 23 (Catalog).
R2 Apex-Posterior Electrode (Brochure).
Atricor Pacer (Brochure).
Ventri-Stat Flare Electrode (Brochure).
"New Stable Temporary Atrial Pacing Loop", 34 American Journal of Cardiology 325, Sep., 1974, Berens et al.
"Automatic Implantable Defibrillator", Pacemaker Therapy, p. 195, Mirowski et al.

Primary Examiner—Lee S. Cohen
Assistant Examiner—K. Schaetzle
Attorney, Agent, or Firm—Limbach, Limbach & Sutton

[57] ABSTRACT

A method and apparatus for implanting an automatic implantable defibrillator without the need for major surgery is disclosed. Preconfigured electrodes are straightened by the use of a stylet or by the surrounding catheter and inserted into the intrapericardial space through catheters. The catheters may be removed or may be left in place and attached to the pericardium or surrounding tissue to hold the electrodes in place.

4 Claims, 5 Drawing Sheets

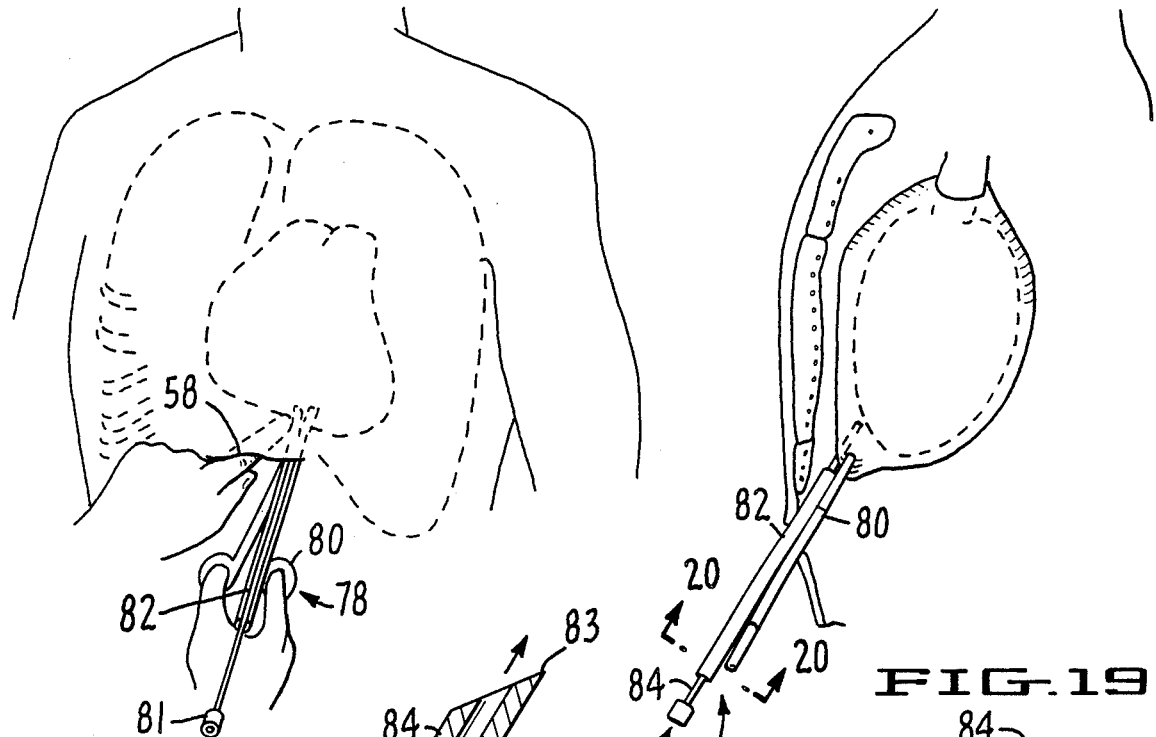
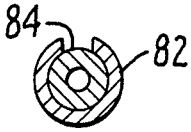
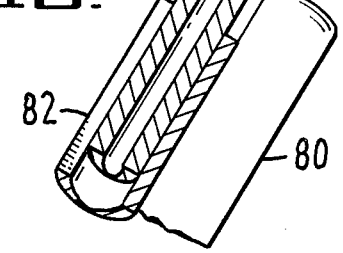
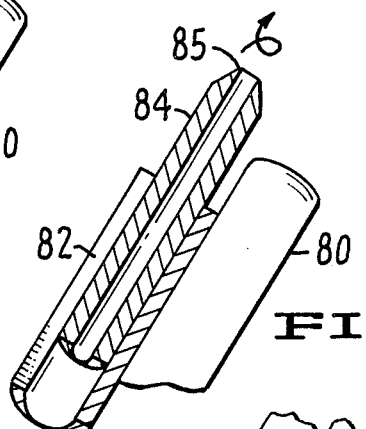
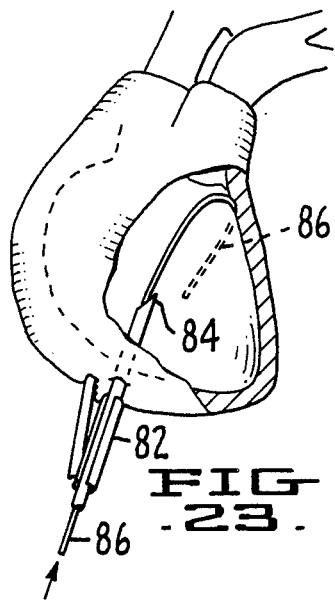
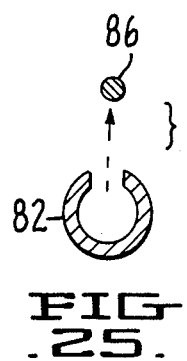

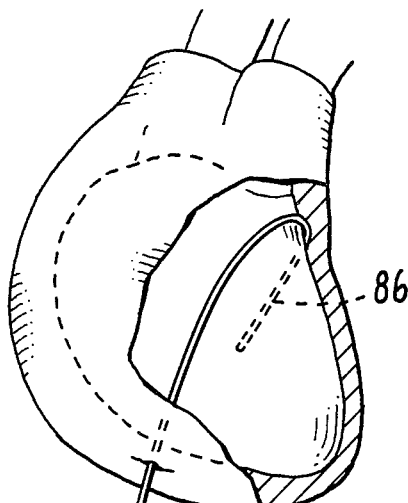
FIG. 26.
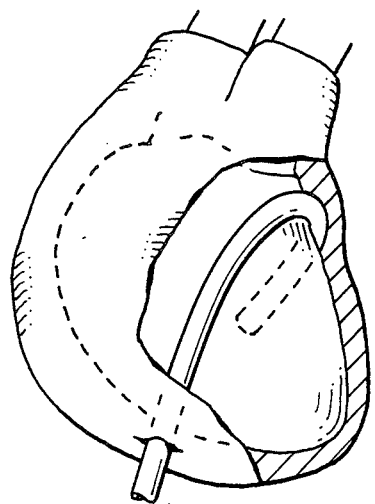
FIG. 27.
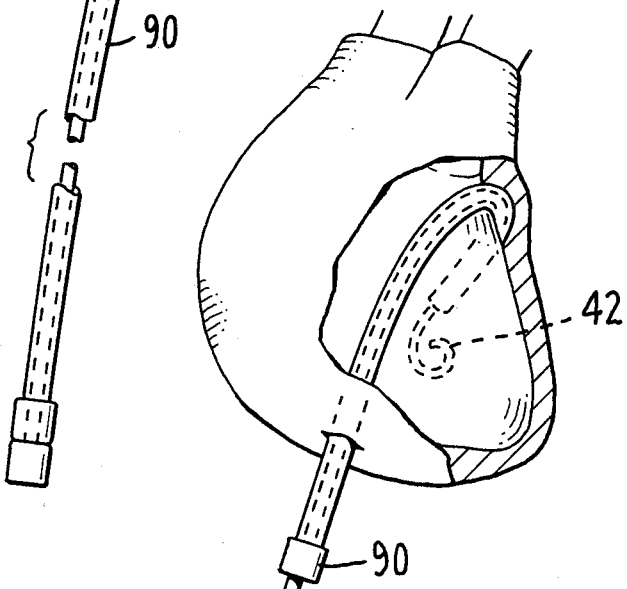
FIG. 28.
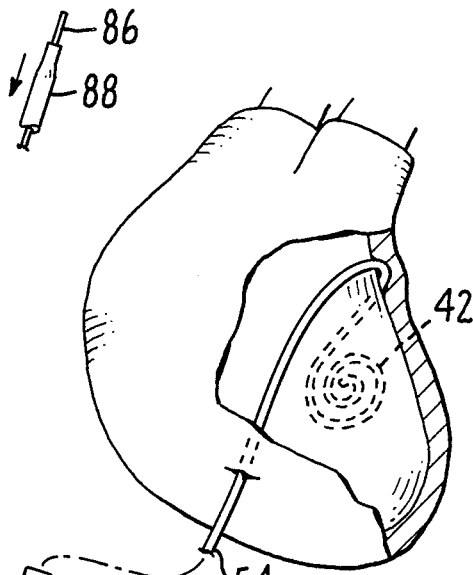
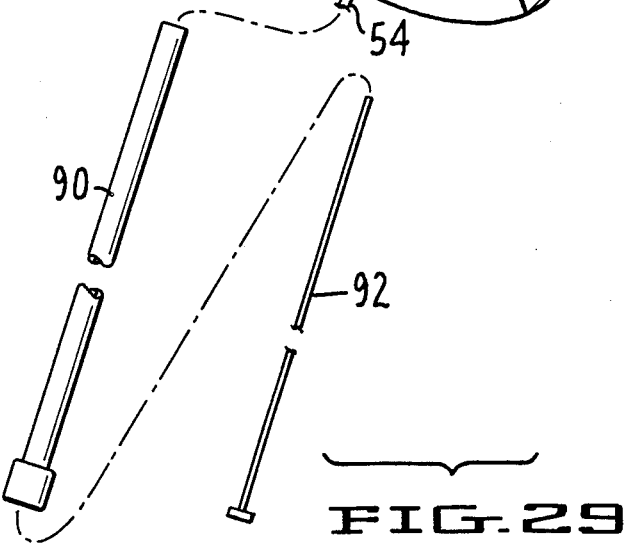
FIG. 29

METHOD FOR IMPLANTING AUTOMATIC IMPLANTABLE DEFIBRILLATOR

BACKGROUND OF THE INVENTION

1. Field of the Invention

This invention relates generally to electrical defibrillation, and relates more specifically to particular types of implantable electrodes and methods of implanting them with a minimal amount of surgery.

It is well known in the field of cardiology that certain types of cardiac arrhythmias known as ventricular tachycardia and fibrillation can be effectively treated by the application of electrical shocks to the heart to defibrillate the fibrillating tissues. Such defibrillation may be achieved by the application by medical personnel of electrical paddles to the chest of the patient or directly to the heart tissue, if the chest is open during surgery.

More recent improvements have led to the development of implantable defibrillators which automatically monitor the heart for arrhythmia and initiate defibrillation when arrhythmia occurs. Such devices typically incorporate electrodes which are located either next to the heart or on an intravascular catheter, or both. Because the electrodes are closer to the heart tissue, implanted defibrillators require less electrical energy to stimulate the heart than external electrodes.

However, major surgery is generally necessary to implant present defibrillator lead systems, such as a median sternotomy or lateral thoracotomy. These procedures can be very traumatic to the patient, and may have adverse side effects such as surgical complications, morbidity or mortality. Because of these risks, only those persons whose condition is so dire that the potential benefits outweigh the risks are suitable candidates for such surgery, thus excluding many patients who might otherwise benefit from the surgery.

2. Description of the Relevant Art

There have been various attempts to solve these problems, such as that of Heilman, U.S. Pat. No. 4,291,707, and Heilman, U.S. Pat. No. 4,270,549, which respectively show an electrode and the method of implanting it. Heilman teaches the use of rectangular paddle electrodes measuring 4 cm. by 6 cm. Two such electrodes are used, requiring in the illustrated embodiments two incisions, one in the abdominal wall and one in the interior thoracic region. Alternatively, one paddle electrode may be inserted through an incision and another intravascular electrode inserted into the superior vena cava. This still requires two separate intrusions into the body, however. Heilman does briefly mention the possibility of inserting both electrodes through a single incision; however, even in this case, that incision must be a long median sternotomy or thoracotomy, such as that commonly performed for an open heart procedure such as a coronary artery bypass, in order to allow passage of the paddles.

Another attempted solution involves the use of bipolar electrodes, i.e. a single assembly that contains both electrodes, so that only that single assembly need be put in contact with the heart tissue. Such electrodes are shown in Ackerman, U.S. Pat. No. Re. 27,569, and Alferness, U.S. Pat. No. 4,355,642. However, it is believed that better results are obtained by locating the electrodes on opposite sides of the heart, either side to side or front to back.

Other types of electrodes, some of which may be used transvenously, are shown in Williamson, U.S. Pat. No. 3,749,101, Kallok et al., U.S. Pat. No. 4,355,646, and Moore, U.S. Pat. No. 4,567,900.

SUMMARY OF THE INVENTION

In accordance with the illustrated preferred embodiment, the present invention provides for passing a first catheter through the pericardial sac and into the intrapericardial space such that it terminates in a position proximate to the heart; inserting a first electrode into the intrapericardial space by sliding it through said first catheter such that the distal end of said first electrode is extended beyond the distal end of said first catheter and is located proximate to the heart; passing a second catheter through the pericardial sac and into the intrapericardial space such that it terminates in a position proximate to the heart; and inserting a second electrode into the intrapericardial space by sliding it through said second catheter such that the distal end of said second electrode is extended beyond the distal end of said second catheter and is located proximate to the heart.

In the preferred embodiment, both catheters and electrodes are inserted in a single incision in the upper abdominal wall, resulting in less trauma to the patient than in procedures requiring two incisions. A fluoroscope may be used to view the heart and assist in placing the electrodes.

The proximate ends of the catheter are attached to the pericardium or the surrounding connective tissue so that the catheters, and thus the electrodes, are held in a nearly fixed position. This prevents the electrodes from migrating as mentioned above, and may be accomplished by use of a "button" which is sutured to the pericardium or surrounding tissue, and which contains in its center a metal ring which may be crimped on the catheter once the correct position has been attained.

In an alternative embodiment, the catheters may be used only to insert the electrodes and then removed, leaving the electrodes in place. In this case, it is preferable to attach the electrodes to the heart tissue or surrounding tissue to prevent migration.

In the preferred embodiment, each electrode is preconfigured such that the distal end assumes a specified configuration, such as a spiral, upon exiting from the distal end of the respective catheter, allowing a cylindrical electrode to approximate the function of a paddle-type electrode. However, other shapes might also be used. The conductive portion of the electrode may be a spiral of metal foil or wire on a non-conductive, generally cylindrical stem, or a wire element contained in the stem and exposed in short cylindrical sections or in a channel along one side of the stem. Applicants have a co-pending application entitled Implantable Defibrillation Electrode on electrodes that may be used with this invention.

The features and advantages described in the specification are not all inclusive, and particularly, many additional features and advantages will be apparent to one of ordinary skill in the art in view of the drawings, specification and claims hereof. Moreover, it should be noted that the language used in the specification has been principally selected for readability and instructional purposes, and may not have been selected to delineate or circumscribe the inventive subject matter, resort to the claims being necessary to determine such inventive subject matter.

BRIEF DESCRIPTION OF THE DRAWINGS

FIG. 18 shows the first step of the alternative embodiment of making an incision in the upper abdominal wall and inserting a tool therein.

FIG. 19 is a side view of the body after insertion of the tool into the pericardial sac.

FIG. 20 is a view of the channel portion of the tool taken along line 20—20 in FIG. 19.

FIG. 21 is a side view of the tool and shows the prior step of inserting the pointed end of the tool into the pericardial sac.

FIG. 22 is a side view of a different embodiment of the tool with a different cutting end thereon.

FIG. 23 shows the next step of the alternative embodiment wherein a guide wire is inserted through the center section of the tool.

FIG. 24 shows the next steps of the alternative embodiment wherein the center section of the tool is removed and the guide wire is removed from the channel portion of the tool.

FIG. 25 shows an end view of the step of removing the guide wire from the channel portion of the tool.

FIG. 26 shows the next step of the alternative embodiment wherein a catheter having a dilating member is inserted over the guide wire and into the pericardial sac.

FIG. 27 shows the next step of the alternative embodiment wherein the dilating member is removed from the catheter.

FIG. 28 shows the next step of the alternative embodiment wherein a preconfigured electrode which is straightened by a stylet is inserted through the catheter such that the distal end is positioned on the posterior surface of the heart.

FIG. 29 shows the next step of the alternative embodiment wherein the catheter and the stylet are withdrawn, leaving the electrode in place.

DETAILED DESCRIPTION OF THE PREFERRED EMBODIMENT

FIGS. 1 through 29 of the drawings depict various preferred embodiments of the present invention for purposes of illustration only. One skilled in the art will readily recognize from the following discussion that alternative embodiments of the structures and methods illustrated herein may be employed without departing from the principles of the invention described herein.

Figure 1:
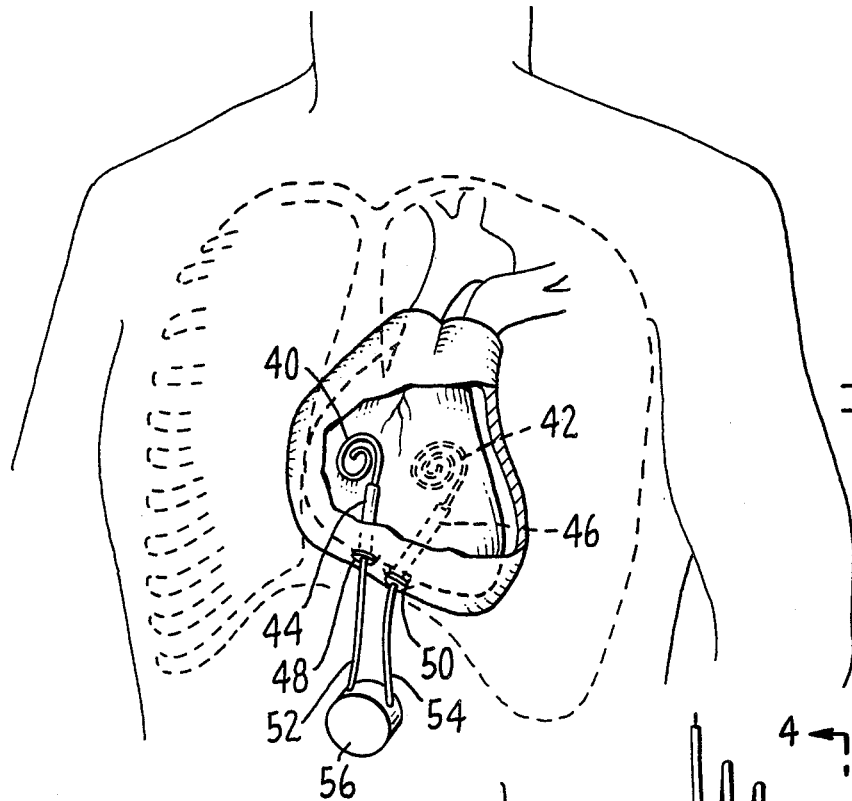
FIG. 1 is a sectional view of a body showing a defibrillator implanted according to the preferred embodiment of the present invention.
Figure 2:
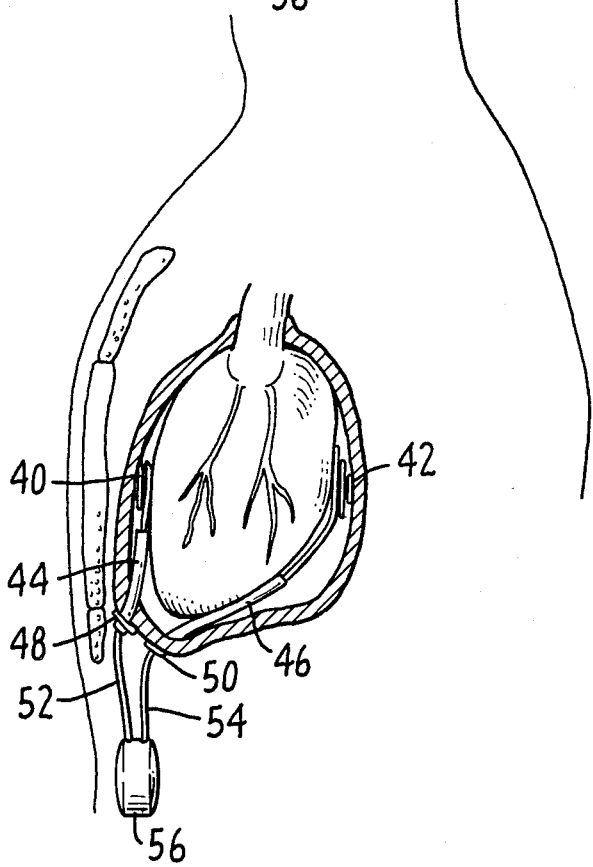
FIG. 2 is a cross-sectional side view of the body of FIG. 1.
Figure 16:
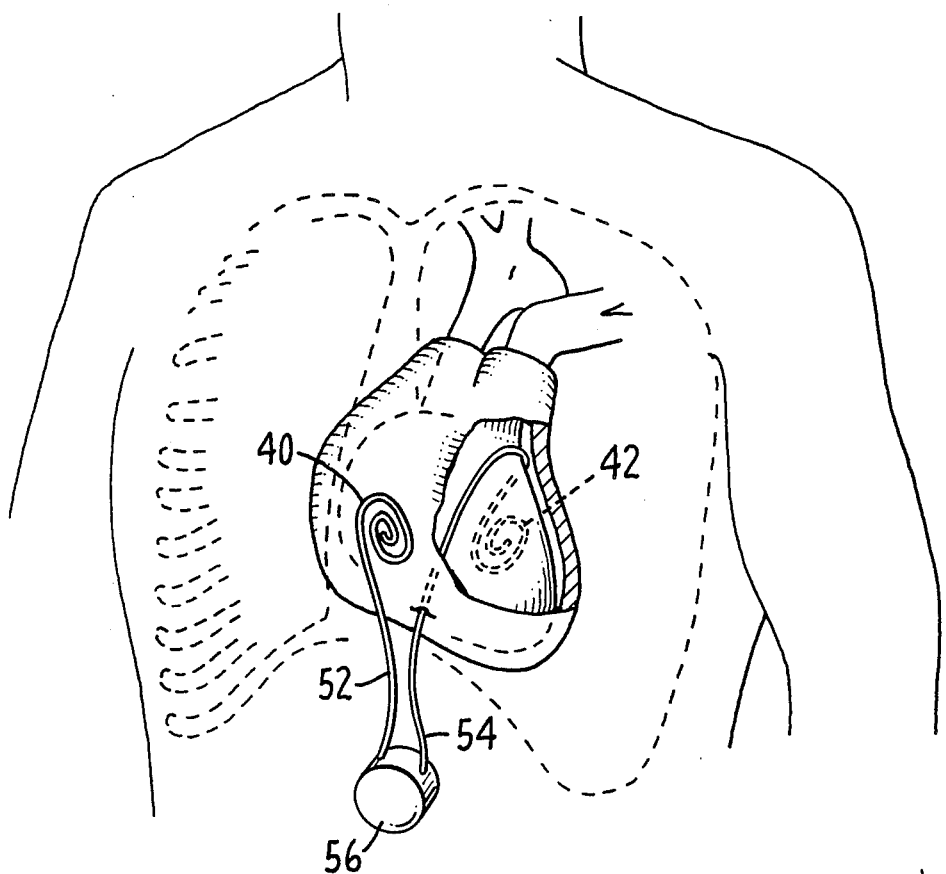
FIG. 16 is a sectional view of a body showing a defibrillator implanted according to an alternative embodiment of the present invention.
Figure 17:
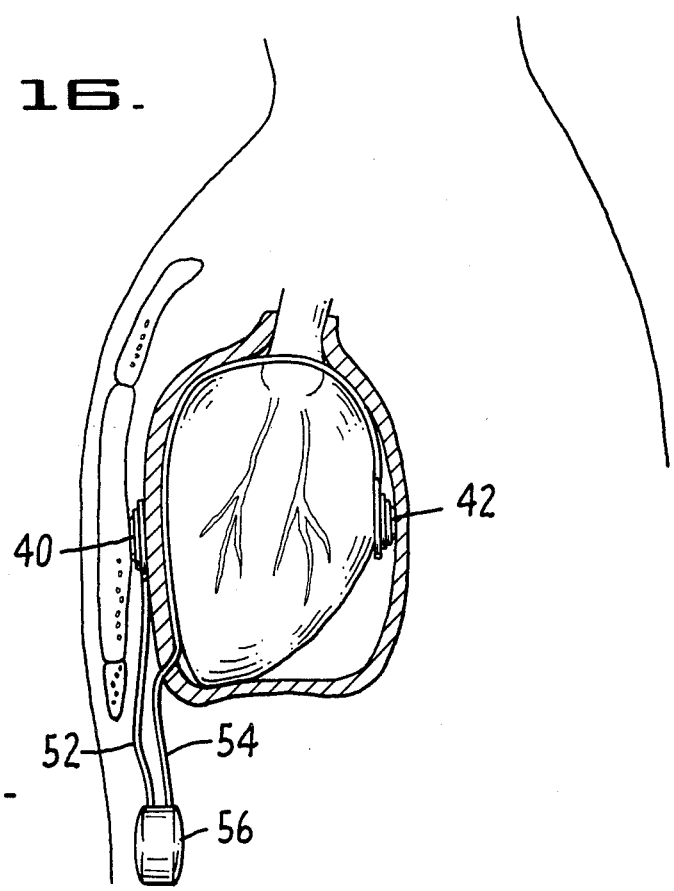
FIG. 17 is a cross-sectional side view of the body of FIG. 16.

A defibrillator installed by the method of the present invention is shown in FIGS. 1 and 2. FIGS. 3 through 6 show various shapes of electrodes that may be used. The preferred embodiment of the method of installing the defibrillator is detailed in FIGS. 7 through 15. FIGS. 16 and 17 show a defibrillator installed pursuant to an alternative embodiment of the method of the present invention, and FIGS. 18 through 29 detail that alternative embodiment.

In FIG. 1, the defibrillator is shown after implantation, with the electrodes 40 and 42 located on the anterior and posterior surfaces of the heart respectively. The electrodes are held in place by two cannulae, or catheter sections, 44 and 46, which are in turn held by two fastening buttons 48 and 50 which are sewn to the pericardium or surrounding connective tissue. The electrode leads 52 and 54 are attached to the implanted defibrillator module 56.

Figure 3:
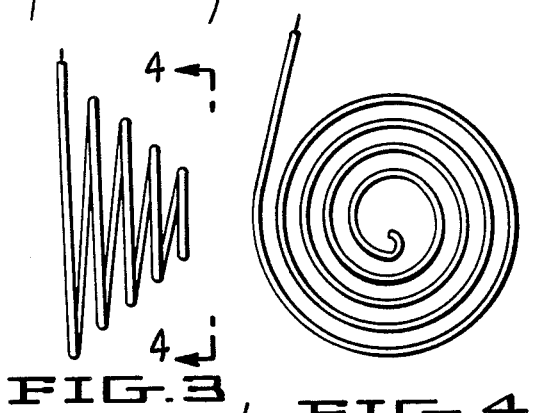
FIG. 3 is a side view of an electrode showing one possible configuration that may be used with the present invention.
Figure 4:
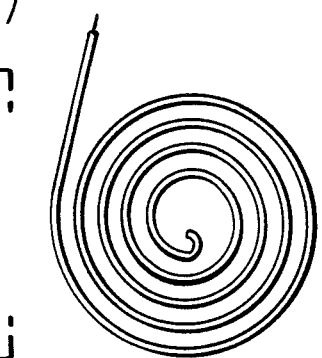
FIG. 4 is a top view of the electrode of FIG. 3 taken along the line 4—4 of FIG. 3.

The electrodes may be of various shapes, as shown in FIGS. 3 through 6. In the preferred embodiment, the electrode is preconfigured as a spiral in order to increase the contact area and thus simulate the function of a paddle electrode. In FIG. 3 the spiral is a conical one which does not lie in a single plane but spirals upward as it spirals inward. FIG. 4 is a top view of this electrode, taken along line 4—4 in FIG. 3. This three-dimensional coil gives the electrode a spring effect between the heart surface and the pericardium which tends to keep the electrode in place.

Figure 5:
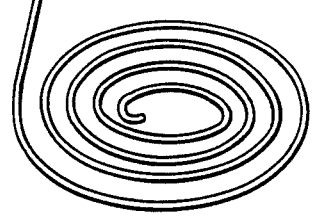
FIG. 5 is an elevational view of an electrode showing another configuration that may be used with the present invention.
Figure 6:
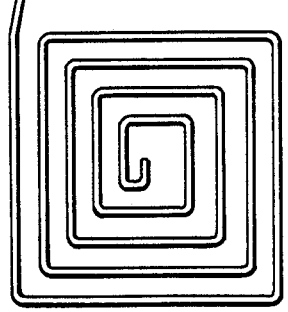
FIG. 6 is a top view of an electrode showing another configuration that may be used with the present invention.

Alternatively, a flat spiral shape may be used for the electrode. In FIG. 5 a flat round spiral electrode is shown. In FIG. 6, an electrode having a "square spiral" shape is shown.

Figure 7:
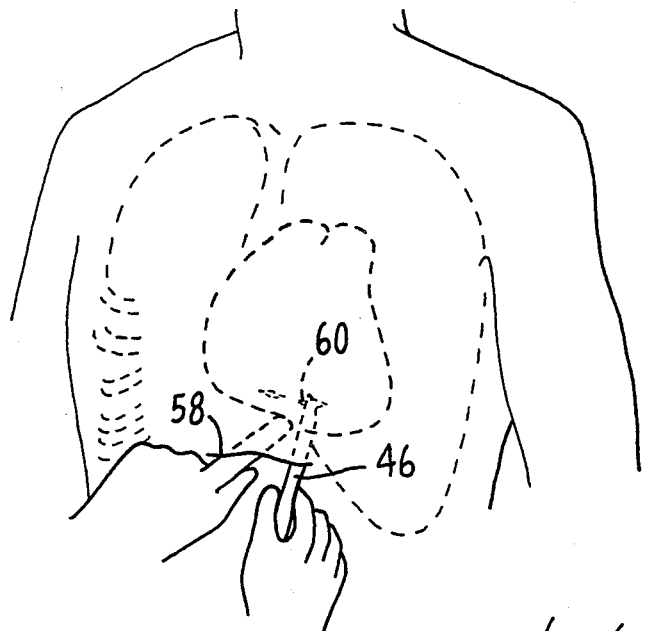
FIG. 7 shows the first step of the preferred embodiment of making an incision into the upper abdominal wall and inserting a first catheter into the intrapericardial space.

FIG. 7 shows the first step of the preferred embodiment of the method of the present invention. An incision 58 is made in the upper abdominal wall of the patient; the tissues between this incision 58 and the pericardium of the patient are separated digitally by spreading of the surgeon's fingers, and another incision 60 is made in the pericardium. The cannulus 46 is inserted into the pericardial sac through these incisions.

Figure 8:
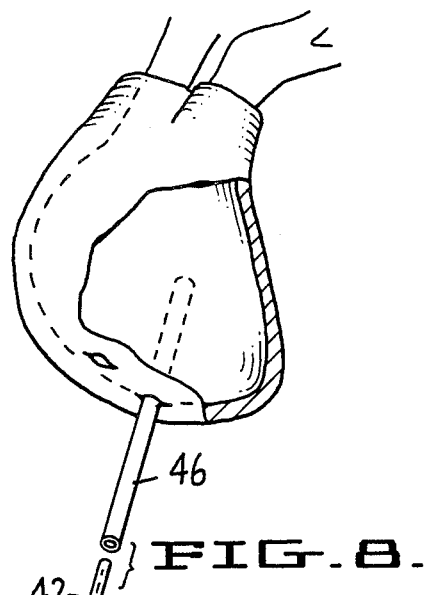
FIG. 8 shows the subsequent step of inserting a preconfigured first electrode into the first catheter, with a stylet inside the electrode.
Figure 9:
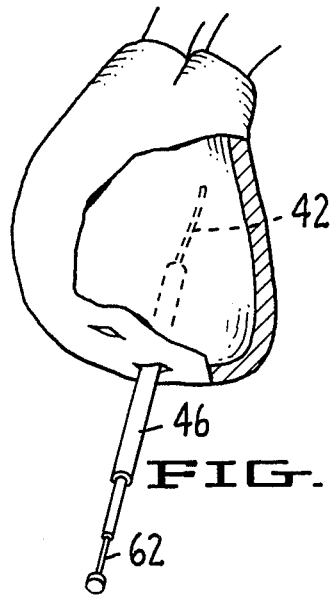
FIG. 9 shows the first electrode after insertion through the first catheter.
Figure 10:
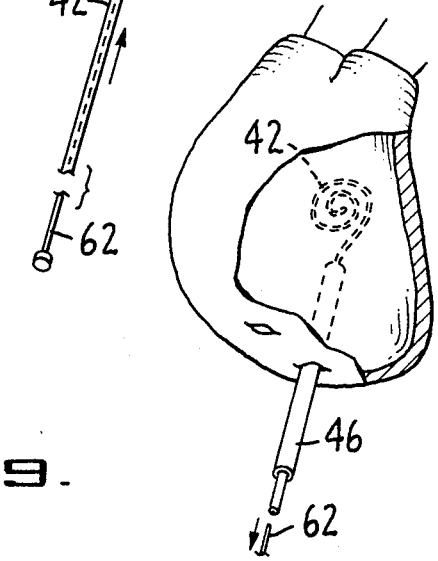
FIG. 10 shows the subsequent step of removing the stylet.

The preconfigured electrode 42 is then inserted into the pericardium through the cannulus 46 to the posterior of the heart, as shown in FIG. 8. To increase the ease of insertion of the electrode, a stylet 62 is inserted into the electrode to straighten it before insertion. The distal end of the electrode 42 is extended beyond the end of the cannulus 46, as shown in FIG. 9, and the stylet 62 is then removed, allowing the electrode 42 to assume its preconfigured shape. The resulting position is shown in FIG. 10.

Figure 11:
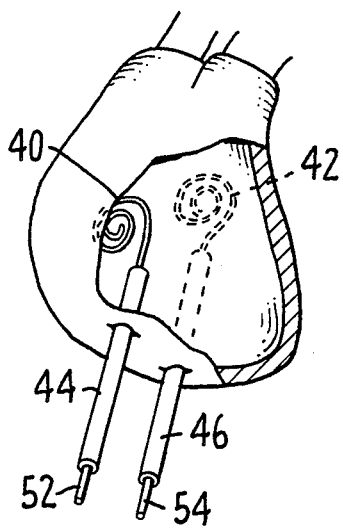
FIG. 11 shows both electrodes and catheters after insertion.

The other cannulus 44 and corresponding electrode 40 is inserted in the same manner, but on the opposite side (anterior) of the heart, resulting in the position shown in FIG. 11. Electrode leads 52 and 54 extend from the ends of the cannulae 44 and 46.

Figure 12:
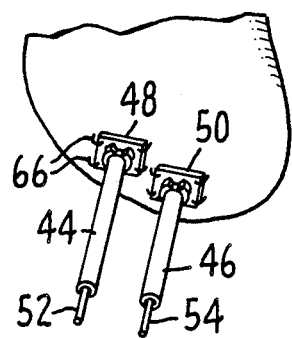
FIG. 12 shows the proximal ends of both catheters and electrodes after attachment and crimping of the fastening buttons.
Figure 13:
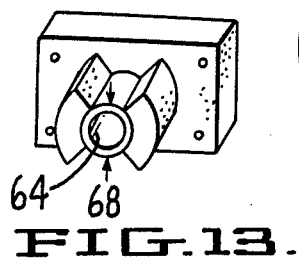
FIG. 13 is a perspective view of a fastening button.

Fastening buttons 48 and 50 are then placed on the cannulae 44 and 46, as shown in FIG. 12, and sewn to the pericardium or surrounding connective tissue with sutures 66. A detailed view of a fastening button is shown in FIG. 13; it contains a channel 64 through which the cannulus passes, and a crimping ring 68 which is made of metal. After the fastening buttons 48 and 50 are sewn in place, the cannulae 44 and 46 are manipulated until the electrodes 40 and 42 are located in the desired positions, and the crimping rings 68 are then crimped with pliers or some other tool such that the cannulae 44 and 46 are fixed in the desired positions. As mentioned above, a fluoroscope may also be used to view the electrodes for assistance in locating them where desired.

Figure 14:
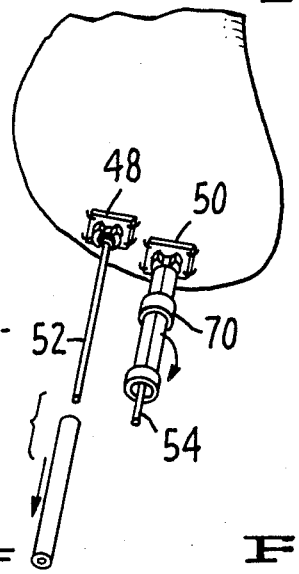
FIG. 14 shows the proximal end of one electrode after removal of the excess portion of the catheter, and the excess portion of the other catheter being removed by the cutting tool.
Figure 15:
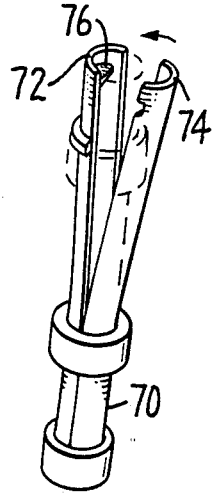
FIG. 15 is a perspective view of the cutting tool.

Next, the excess portions of the cannulae 44 and 46 which extend beyond the heart and the fastening buttons 48 and 50 are removed, as shown in FIG. 14. A cutting tool 70 is used to cut the cannulae 44 and 46 without cutting the electrode leads 52 and 54. Cutting tool 70 is shown in detail in FIG. 15. It includes a hinged cylindrical body comprised of stationary piece 72 and movable piece 74, which is hinged near the proximate end of cutting tool 70. Inside at the distal end is cutting edge 76. In practice, movable piece 74 is opened and cutting tool 70 is slid over one of the cannulae until the distal end is proximate to the fastening button, and the movable piece 74 is then closed. This pins the cannulus in the cutting tool 70 so that it may be cut by cutting edge 76, which extends far enough into the center of cutting tool 70 to cut the cannulus but not the electrode lead. Cutting tool 70 is then rotated to score the cannulus all the way around its circumference. In FIG. 14, cutting tool 70 is shown in place on cannulus 46, next to fastening button 50, with electrode lead 54 extending; the excess portion of cannulus 44 has already been removed, leaving electrode lead 52. The arrow shows that cutting tool 70 is being rotated.

After the excess portions of cannulae 44 and 46 have been removed, electrode leads 52 and 54 may be connected to the defibrillator module 56 and the incision in the body closed.

In using this method, it is also possible to use electrodes which do not incorporate stylets. In this case the spiral is straightened manually and then inserted into the cannula, which keeps the electrode straight until it emerges from the distal end of the cannula, at which point it again assumes a spiral shape.

FIGS. 16 and 17 show a front and side view respectively of an alternative embodiment of the present invention. Electrodes 40 and 42 are connected to defibrillator module 56 through electrode leads 52 and 54. The electrodes may be of the same shapes as in the preferred embodiment. However, there are no cannulae or fastening buttons in this embodiment.

FIG. 18 shows the first step of making an incision 58 in the upper abdominal wall and inserting a forceps tool 78 therein. The forceps tool 78 has a clamping body 80 on which is mounted a channel portion 82. Within the channel portion 82 is a hollow stylet 84 with a proximal end piece 81. Stylet 84 may have a pointed distal end 83 as shown in FIG. 21, or a flat end 85 which is beveled all the way around, as shown in FIG. 22. The stylet 84 is slidable within the channel portion 82, and the distal end 83 or 85 is limited to extending no more than approximately 1 centimeter beyond the distal end of the channel portion 82 by the end piece 81.

The clamping body 80 is used to grasp the pericardium and "tent" it by lifting it away from the heart surface, and the distal end of the stylet 84 is then advanced through the channel portion 82 and used to puncture the pericardium, as shown in FIG. 19. This "tenting" prevents the user from accidentally puncturing the heart itself while the pericardium is punctured, since the distance that the end of the stylet 84 may extend beyond the channel portion 82 is limited by end piece 81. If the end of the stylet 84 is the pointed end 83 of FIG. 21, the puncture may be made by simply advancing the stylet 84, as shown by the arrow in FIG. 21. On the other hand, if the stylet 84 has the beveled end 85 of FIG. 22, it may be necessary to rotate the stylet 84 as shown by the arrow in FIG. 22. FIG. 20 shows an end view of the channel portion 82, with the stylet 84 within, taken along line 20—20 in FIG. 19.

A guide wire 86 is then advanced through the stylet 84, as shown in FIG. 23; in FIG. 23 the wire 86 has been advanced so that its distal end is posterior to the heart. Once the guide wire is in place, the stylet 84 is removed by retracting it, as shown by the arrow in FIG. 24; the wire 86 may then be laterally removed from the channel portion 82 of the forceps tool 78, as shown in FIGS. 24 and 25, and the forceps tool 78 is itself removed, leaving only the guide wire 86 in place.

A two piece catheter is then advanced into the pericardium, as shown in FIG. 26. This catheter is composed of an internal catheter 88 with a tapered tip and an outer catheter body 90. As the internal catheter 88 is advanced, the tapered tip opens the incisions enough to permit passage of the outer catheter body 90. Once the outer catheter body 90 is in place, the guide wire 86 and inner catheter 88 may be.removed, as shown in FIG. 27. As above, here the placement shown is posterior to the heart.

Now electrode 42 may be inserted through catheter 90, as shown in FIG. 28. As in the prior embodiment, a stylet 92 may be used to straighten out the preconfigured electrode 42 to permit easier insertion. If the electrode 42 is to be placed posterior to the heart by going over the shoulder as shown here, the stylet 92 may be somewhat flexible so that the electrode 42 can be pushed as far as the distal end of catheter 90 with the stylet 92 in place. Then, as the electrode 42 is advanced further, it simultaneously exits catheter 90 and assumes its preconfigured shape.

Finally, the stylet 92 and catheter 90 are removed, leaving the electrode 42 in place, as shown in FIG. 29. The electrode lead 54 is connected to the defibrillator module 56. The other electrode 52 is inserted by the same method, but anterior to the heart. (Alternatively, the electrodes may be placed on opposite lateral sides of the heart.) The placing of the electrode 42 posterior to the heart by going over the shoulder of the heart helps to prevent migration. If more security is desired, the electrodes may be sutured in place, or small anchors may be added to the distal ends of the electrodes to anchor them.

From the above description, it will be apparent that the invention disclosed herein provides a novel and advantageous method for implanting an automatic defibrillator. The foregoing discussion discloses and describes merely exemplary methods and embodiments of the present invention. As will be understood by those familiar with the art, the invention may be embodied in other specific forms without departing from the spirit or essential characteristics thereof. For example, other shapes of electrodes may be used, and they may be located in other positions, as long as migration is prevented.

Accordingly, the disclosure of the present invention is intended to be illustrative, but not limiting, of the scope of the invention, which is set forth in the following claims.

What is claimed is:

1. A method for implanting an automatic defibrillator in a human and placing it proximate to the heart, comprising the steps of:

passing a first catheter through the pericardial sac and into the intrapericardial space such that it terminates in a distal end positioned proximate to the heart;

inserting a first electrode having proximal and distal ends into the intrapericardial space by sliding it through said first catheter such that the distal end of said first electrode is extended beyond the distal end of said first catheter and is located proximate to the heart;

passing a second catheter through the pericardial sac and into the intrapericardial space such that it terminates in a distal end positioned proximate to the heart;

inserting a second electrode having proximal and distal ends into the intrapericardial space by sliding it through said second catheter such that the distal end of said second electrode is extended beyond the distal end of said second catheter and is located proximate to the heart; and, fastening the first and second catheters to the pericardium or the surrounding connective tissue such that the catheters and the electrodes are held in a generally fixed position.

2. A method according to claim 1 wherein the step of fastening the first and second catheters to the pericardium or the surrounding connective tissue comprises the steps of:

sliding over said first and second catheters first and second fastening buttons each having a central opening in which is disposed a crimping ring large enough to fit over the respective catheter;

attaching said buttons to the pericardium or the surrounding connective tissue; and crimping each of said crimping rings enough to firmly grasp the catheter located within it without severing the electrode located within the catheter.

3. A method according to claim 1 wherein the first electrode is a preconfigured hollow electrode, and further comprising the step of inserting a stylet into the hollow portion of said first electrode prior to insertion into the intrapericaridial space to straighten said first electrode during insertion.

4. A method according to claim 1 wherein the second electrode is a preconfigured hollow electrode, and further comprising the step of inserting a stylet into the hollow portion of said second electrode prior to insertion into the intrapericardial space to straighten said second electrode during insertion.

* * * * *

UNITED STATES PATENT AND TRADEMARK OFFICE
Certificate

Patent No. 4,865,037                                                                  Patented: Sept. 12, 1989

On petition requesting issuance of a certificate for correction of inventorship pursuant to 35 U.S.C. 256, it has been found that the above-identified patent, through error and without any deceptive intent, improperly sets forth the inventorship. Accordingly, it is hereby certified that the correct inventorship of this patent is:
Albert K. Chin, Thomas J. Fogarty and Eric S. Fain.

Signed and Sealed this Twenty-fifth Day of December, 1990.

K. SCHAETZLE

*Assistant Examiner*
*Art Unit 335*